United States Patent [19]

Matsuda et al.

[11] Patent Number: 5,447,920
[45] Date of Patent: Sep. 5, 1995

[54] COSMETIC COMPOSITION CONTAINING INCLUSION PRODUCT WITH HYDROXYALKYLATED CYCLODEXTRIN

[75] Inventors: Hajime Matsuda; Kenzo Ito, both of Yokohama; Akio Taki; Osamu Uejima, both of Mishima, all of Japan

[73] Assignee: Shiseido Company Ltd., Tokyo, Japan

[21] Appl. No.: 186,403

[22] Filed: Jan. 25, 1994

Related U.S. Application Data

[63] Continuation of Ser. No. 855,163, Mar. 20, 1992, which is a continuation of Ser. No. 427,170, Oct. 26, 1989, abandoned.

[30] Foreign Application Priority Data

Oct. 28, 1988 [JP] Japan .................. 63-272653

[51] Int. Cl.⁶ ............. A61K 7/42; A61K 7/46; A61K 7/48; A61K 31/715
[52] U.S. Cl. .................. 514/58; 424/59; 424/60; 424/401; 424/489; 514/844; 514/845; 514/846; 514/847; 514/848
[58] Field of Search ............ 514/58, 844, 845, 846, 514/847, 848; 536/103; 424/401, 59, 60, 489

[56] References Cited

U.S. PATENT DOCUMENTS

| | | | |
|---|---|---|---|
| 3,459,731 | 8/1969 | Gramera et al. | 536/103 |
| 4,722,815 | 2/1988 | Shibanai | 536/103 |
| 4,727,064 | 2/1988 | Pitha | 514/58 |
| 4,764,604 | 8/1988 | Müller | 536/103 |
| 4,834,985 | 5/1989 | Elger et al. | 424/488 |
| 4,883,785 | 11/1989 | Chow et al. | 514/58 |
| 5,256,652 | 10/1993 | El-Rashidy | 514/58 |

FOREIGN PATENT DOCUMENTS

| | | |
|---|---|---|
| 0121777 | 10/1984 | European Pat. Off. . |
| 61-109705 | 5/1986 | Japan . |
| WO85/02767 | 7/1985 | WIPO . |

OTHER PUBLICATIONS

Yoshida et al, International Journal of Pharmaceuticals, vol. 46, (1988), pp. 217–222.
Chemical Abstracts, vol. 109, 1988, Abstract 109:236840u.
Frank, Journal of Pharmaceutical Sciences, vol. 64, No. 10, Oct. 1975, pp. 1585–1604.
Saenger, Angew. Chem. Int. Ed. Engl., vol. 19, pp. 344–362 (1980).
Szejtli (Die Nahrung, vol. 29, No. 9, pp. 911–924 (1985).
J. Szejtli, Proceedings of the First International Symposium on Cyclodextrins, pp. 467–477 (1981), D. Reidel Publishing Co., Boston, U.S.A.
Szejtli, Controlled Drug Bioavailability, 1985, vol. 3, Chapter 8, pp. 365–420.
Pitha et al., International Journal of Pharmaceutics, vol. 29, (1986), pp. 73–82.

*Primary Examiner*—Ronald W. Griffin
*Attorney, Agent, or Firm*—Sprung Horn Kramer & Woods

[57] ABSTRACT

A cosmetic composition comprising an inclusion product having a slightly water-soluble component with a hydroxyalkylated cyclodextrin formulated therein.

9 Claims, No Drawings

COSMETIC COMPOSITION CONTAINING INCLUSION PRODUCT WITH HYDROXYALKYLATED CYCLODEXTRIN

This application is a continuation of application Ser. No. 07/855,163, filed Mar 20, 1992, now pending, which is a continuation of Ser. No. 07/427,170, filed Oct 26, 1989, now abandoned.

BACKGROUND OF THE INVENTION

1. Field of Invention

The present invention relates to a cosmetic composition including a liquid and powdery cosmetic compositions comprising an inclusion product having a slightly water-soluble component with ah hydroxyalkylated cyclodextrin (hereinafter abbreviated as "HACD") formulated therein. More specifically, the present invention relates to a liquid cosmetic composition and a powdery cosmetic composition having improved product characteristics such as useability and stability, and effectively preventing skin roughening, due to the formulation of an inclusion product with HACD.

2. Description of the Related Art

Cosmetic compositions well known in the art such as cosmetic water, lotions, beauty lotion, etc. contain, in addition to a main component such as water or alcohol, various slightly water-soluble components such as oils and fats, physiologically active substances, UV-ray absorbers, antiphlogistics, and perfumes, formulated by utilizing a small amount of a surfactant for enhancing the useability and utility thereof.

Also, powdery cosmetic compositions used for an amelioration of skin sorenes dure to a sunburn contain a slightly water-soluble component such as a skin activator and a drug in a water-soluble powdery base.

In cosmetic compositions, it is well known that a quantitative limitation will arise when formulating the above-mentioned slightly water-soluble components, and therefore, for example, when solubilizing slightly water-soluble components in large amounts and in a uniform state, a large amount of ethanol or a polyol must be formulated, but the formulation of these components cause the problem of skin irritation. Also, if the slightly water-soluble components are not uniformly dissolved, a problem arises in that the cosmetic composition becomes turbid or loses its transparency, to thereby reduce its commercial value. Further, the slightly water-soluble components formulated also react with the other components, to thereby cause a deterioration and decomposition of the other components.

To solve these problems, Japanese Unexamined Patent Publication (Kokai) No. 61-227517 discloses a technique by which the above-mentioned components are formulated by utilizing the inclusion action of a cyclodextrin polymer. But, according to this method, since a cyclodextrin polymer per se having a constant quality is difficult to obtain, and because the polymer is viscous and slightly soluble in water, satisfactory results could not be obtained.

Also, in powdery cosmetic compositions of the type which are commercially available in powdery form, to which water is added before use, since this type of cosmetic is solubilized between the palms while using only of a small amount of water, the slightly water-soluble components are not uniformly dissolved, and therefore, a coarse feeling remains during use and; the pharmacological effect thereof is not fully exhibited. As means for solving these problems, attempts have been made to increase the amount of the surfactant or to utilize the inclusion action of a cyclodextrin polymer, but good results could not be obtained for the same reason as mentioned above. Also, none of the cyclodextrin polymers provides a satisfactory skin roughening prevention effect.

Recently, there is a trend toward using a base makeup on the skin, primarily directed to beautifying the skin, and thus there is a need for a cosmetic composition which effectivly prevents skin roughening and retains the preferable characteristics of a cosmetic composition.

SUMMARY OF THE INVENTION

Accordingly, the objects of the present invention are to eliminate the above-mentioned disadvantages of the prior art and to provide a cosmetic composition having a high degree of safety, an excellent solubility, useability, and stability, and providing an effective skin roughening prevention, by utilizing the inclusion action of HACD, which can be readily solubilized without using a large amount of a solubilizing agent such as ethanol or a polyol.

Other objects and advantages of the present invention will be apparent from the following description.

In accordance with the present invention, there is provided a cosmetic composition comprising an inclusion product having a slightly water-soluble component with a hydroxyalkylated cyclodextrin formulated therein.

DESCRIPTION OF THE PREFERRED EMBODIMENTS

The HACD used in the present invention is a cyclodextrin well known in the art as a cyclic oligosaccharide, having a hydroxyalkyl group introduced into the hydroxyl group thereof.

As the hydroxyalkyl group, substituents such as hydroxymethyl, hydroxyethyl, hydroxypropyl, and hydroxybutyl can be used, and as a result of the reactions of these substituents, an HACD such as hydroxymethyl cyclodextrin, hydroxyethyl cyclodextrin, hydroxypropyl cyclodextrin, and hydroxybutyl cyclodextrin can be obtained.

Cyclodextrin (hereinafter abbreviated as "CD") is known to include CD having $\alpha$, $\beta$ and $\gamma$ structures, (hereinafter abbreviated as "$\alpha$-CD", "$\beta$-CD" and "$\gamma$-CD"), depending on the difference in the glucose number, and in the present invention, one or more of these cyclodextrins can be used after hydroxyalkylation. Also, a starch decomposed product containing $\alpha$, $\beta$, and $\gamma$ CD's can be used at the same time.

These HACD's have an excellent solubility in hydrophilic solvents such as water, compared with the CD of the prior art as shown in Table 1, and in the present invention any desired amount of a slightly water-soluble component can be formulated in a cosmetic composition by utilizing this property and the inclusion action of HACD.

TABLE 1

| Sample | Water | Water/Methanol 50/50 | Water/Methanol 0/100 | Water/Ethanol 50/50 | Water/Ethanol 0/100 | Water/Acetone 50/50 | Water/Acetone 0/100 |
|---|---|---|---|---|---|---|---|
| β-CD | 1.85 | 0.3 | — | 1.3 | — | 2.6 | — |
| Hydroxyethyl β-CD | 57 | 280 | 75 | 250 | <1 | 230 | <1 |
| Hydroxypropyl β-CD | 115 | 87 | 93 | 162 | <1 | 75 | <1 |
| Hydroxypropyl CD mixture | 337 | 325 | <1 | 300 | <1 | 285 | <1 |

Remarks: Numerical values in Table indicate grams dissolved per 100 ml of solvent Of these HACD's, when the cost, production ease, useability and water solubility are taken into consideration, preferably, hydroxyethylated CD or hydroxypropylated CD, more preferably hydroxyethylated β-CD or hydroxypropylated β-CD is used, but the present invention is by no means limited thereto.

Also, the hydroxyethylated CD or hydroxypropylated CD are produced as mixtures of α, β and γ CD's, but such a mixture or an isolated product of an α, β and γ hydroxypropylated CD can be used.

Several processes for preparing HACD are known in the prior art, and an example thereof is shown below.

A 100 g amount of β-CD (manufactured by Nihon Shokuhin Kako, tradename: Seldex N) was dissolved in 150 ml of a 20% aqueous NaOH, 50 ml of propylene oxide was gradually added dropwise while maintaining the temperature at 30° C., and the reaction was continued for 20 hours under stirring. After completion of the reaction, the pH was adjusted to 6.0 with hydrochloric acid, and the product placed in a dialyzing film tube to effect desalting under running water for 24 hours. Then the product was dried by a lyophilizer, to give about 90 g of a propylated β-cyclodextrin. The degree of substitution of the hydroxypropylated β-cyclodextrin was found to be 5.1.

The slightly water-soluble component to be used in the present invention means a cosmetic component which is substantially insoluble or only slightly soluble in water. Specific examples include, for example, natural animal and vegetable oils and fats such as macadamia nut, evening primrose oil, olive oil, mink oil, jojoba oil, lanolin, and squalene; hydrocarbons such as fluid paraffin, squalene; waxes such as paraffin wax, whale wax, beeswax, candelilla wax, and carunauba wax; higher alcohols such as cetanol, isocetanol, stearyl alcohol, and isostearyl alcohol; higher fatty acids such as myristic acid, palmitic acid, stearic acid, behenic acid, isostearic acid, oleic acid, linolenic acid, and linoleic acid oxyacid; fatty acid esters such as isopropyl myristate, isopropyl palmitate, isopropyl isostearate, and glyceryl 2-ethylhexanoate; polar oils such as diethylene glycol monopropyl ether, polyoxyethylene polyoxypropylene pentaerythritol, polyoxypropylene butyl ether, and ethyl linoleate; and silicone oils; and the like.

Further, there may be included vitamins and vitamin-like acting substances such as vitamin A, vitamin D, vitamin E, tocopherol acetate, and ascorbate, and g-oryzanol and folic acid; hormones such as estradiol benzoate, estradiol valerate, ethynyl estradiol, prostaglandin, and testosterone propionate; UV-ray absorbers such as benzophenone, 4-t-butyl-4'-methoxydibenzoylmethane, glyceryl dimethoxycinnamate ethylhexanoate, p-aminobenzoate, octyl p-methoxycinnamate, and phenyl salicylate; antiphlogistics such as L-menthol and camphor; preservatives such as ethyl p-benzoate, propyl p-benzoate, and butyl p-benzoate; and sterilizers such as glycyrrhizinic acid, triclosane, and dibutylhydroxy toluene. Also, there can be included oil-soluble dyes such as Oil Red, Naphthol Yellow, Tartrazine, and Puplika; single substance perfumes such as linalool, linalyl acetate, limonene, citral, methylionone, benzyl acetate, methyldehydrojasmonate, phenylethyl alcohol, muskketone, santalol, a-hexylcinnamicaldehyde, TEC, and citronelol, and composed perfumes comprising mixtures thereof; essential oils derived from natural animal and vegetable oils and fats, and galenicals.

The property of these substances may be either liquid or crystalline, and they may be used either alone or in the form of a mixture.

When preparing the inclusion product using such a slightly water-soluble component and HACD, the well-known methods as described below may be employed.

To an aqueous 20 to 60% by weight of HACD is added and mixed 0.01 to 0.15 part by weight of the required component as mentioned above per 1 part by weight of HACD, followed by stirring and mixing at 20° to 50° C. The stirring may be carried out at 50 to 3000 rpm, and the inclusion reaction time is 2 to 8 hours.

The inclusion product thus obtained is solubilized or emulsified in the aqueous solution, and can be used as such, but the aqueous solution can be also finely powdered by a treatment such as freeze drying or spray drying before use. In the liquid or non-powdery cosmetic composition according to the first embodiment of the present invention, a formulation is possible in either the the reaction mixture or the finely powdered state.

The content of the above-mentioned inclusion product in the liquid cosmetic composition of the present invention, which is influenced by the kind of slightly water-soluble component included and the type of cosmetic composition, is preferably up to 25% by weight, more preferably 0.5 to 15% by weight of the entire cosmetic composition in the finely powdered state. Although it is technically possible to formulate an amount of more than 25% by weight, a drawback arises in that the cosmetic composition becomes sticky during use.

The liquid or non-powdery cosmetic composition of the first embodiment of the present invention, in addition to the above components, can further formulate other conventional cosmetic components corresponding to the commercial product feature, for example, humectants such as hyaluronic acid; water-soluble drugs such as vitamin C; viscosity controllers; pH controllers; preservatives; sterilizers, antioxidants; perfumes; and dyes.

In the powdery cosmetic composition of the second embodiment of the present invention, the same inclusion product as used in the cosmetic composition of the first embodiment of the present invention can be used, but since the dried product form is maintained until immediately before use, preferably the inclusion product of HACD is added in the dry state to other water-soluble base components. The amount of the inclusion product of HACD in the powdery cosmetic composition is preferably up to 50% by weight, more preferably 1.0 to 40%, of the entire powderey cosmetic in the finely powdered state. Although no substantial problem arises with an amount of more than 50% by weight, the cosmetic does become sticky during use.

In the powdery cosmetic composition of the second embodiment of the present invention, soluble powder bases such as D-mannitol and lactose other than the inclusion product of HACD, and corresponding to the commercial product feature, other cosmetic components, for example, humectants such as hyaluronic acid; water-soluble drugs such as vitamin C; viscosity controllers; pH controllers; preservatives; sterilizers; antioxidants; perfumes; and dyes can be also formulated.

According to the present invention, slightly water-soluble components which can be limitedly formulated in the prior art can be formulated in any desired amount without the aid of alcohol, whereby liquid or powdery cosmetic compositions are obtained which have an excellent transparency, stability, safety, useability, and effectively prevent skin roughening. Also, in the present invention, since the slightly water-soluble substance is included with HACD, other components in the liquid or powdery cosmetic compositions are not affected thereby, and thus a long term stabilization is obtained.

Further, in the second aspect of the present invention, an effect is obtained whereby the powdery cosmetic composition is completely dissolved with a small amount of water during use.

EXAMPLES

The present invention will now be further illustrated in detail by, but is by no means limited to, the follwing Examples, wherein "parts" in the formulation are all by weight unless otherwise noted.

EXAMPLE 1

Humectant Cosmetic Water

| Preparation 1 | |
|---|---|
| (1) Hydroxypropylated CD mixture | 2.5 parts |
| (2) Macadamia nut oil | 0.5 parts |
| (3) Vitamin E acetate | 0.05 parts |
| (4) Deionized water | 40 parts |
| Preparation 2 | |
| (1) Deionized water | 39.729 parts |
| (2) Sorbitol | 5 parts |
| (3) 1,3-Butylene glycol | 12 parts |
| (4) Lactic acid | 0.02 parts |
| (5) Sodium lactate | 0.1 parts |
| (6) Monoammonium glycyrrhzinate | 0.1 parts |
| (7) Dye | 0.001 parts |

Preparation Method

The hydroxpropylated CD mixture of (1) (2.5 g) was dissolved in 40 g of deionized water, (2) and (3) were added thereto, and the mixture was stirred to obtain the Preparation 1 containing the inclusion product of the hydroxypropylated CD mixture.

Then the above Preparation 1 was added to the above Preparation 2 to obtain a humectant cosmetic water having a drug stably formulated therein.

When the hydroxypropylated CD mixture was omitted from the above-described composition, the resultant cosmetic water did not have a good stability, in that the oil components were separated from the drug over a lapse of time.

EXAMPLE 2

Systemic Lotion

| Preparation 1 | |
|---|---|
| (1) Hydroxypropylated $\beta$-CD | 5.0 parts |
| (2) Benzophenone | 0.05 parts |
| (3) 4-t-Butyl-4'-methoxy-dibenzoylmethane | 0.01 parts |
| (4) Glyceryl dimethoxycinnamate ethylhexanoate | 0.01 parts |
| (5) Deionized water | 2.0 parts |
| Preparation 2 | |
| (1) Deionized water | 49.8699 parts |
| (2) PEG 400 | 1.0 parts |
| (3) Hinokitiol | 0.01 parts |
| (4) Luffa extract | 1.0 parts |
| (5) Iris extract | 1.0 parts |
| (6) Modified 95% ethanol | 40.0 parts |
| (7) Perfume | 0.05 parts |
| (8) Dye | 0.0001 parts |

Preparation Method

To a solution of (1) dissolved in deionized water were added UV-ray absorbers (2), (3) and (4), followed by stirring, to prepare the Preparation 1 containing the inclusion product of hydroxypropylated $\beta$-CD.

Then the above Preparation 1 was added to the Preparation 2 to obtain a systemic lotion having UV-ray absorbers stably formulated therein.

When the hydroxypropylated $\beta$-CD was omitted from the above-described composition, lotion had a poor stability, in that the UV-absorbers were separated over a lapse of time.

EXAMPLE 3

Essence

| Preparation 1 | |
|---|---|
| (1) Hydroxypropylated $\alpha$-CD | 10 parts |
| (2) Evening primrose oil | 0.2 parts |
| (3) $\alpha$-Tocopherol | 0.05 parts |
| (4) Deionized water | 20 parts |
| Preparation 2 | |
| (1) Deionized water | 59.26 parts |
| (2) Dipropylone glycol | 5 parts |
| (3) Maltitol | 5 parts |
| (4) Aspartic acid | 0.04 parts |
| (5) L-Arginine | 0.1 parts |
| (6) Sodium hexametaphosphate | 0.05 parts |
| (7) Carboxyvinyl polymer | 0.2 parts |
| (8) Perfume | 0.1 parts |

Preparation Method

To a solution of (1) dissolved in deionized water were added (2) and (3), followed by stirring, to prepare the Preparation 1 containing the inclusion product of the hydroxypropylated $\alpha$-CD.

Then the above Preparation 1 was added to the Preparation 2 to obtain an essence having an antioxidant stably formulated therein.

When the hydroxypropylated $\alpha$-CD was omitted from the above-described composition, it was nonuniform and had a poor stability, in that the oil component was separated from the antioxidant over a lapse of time.

EXAMPLE 4

Cosmetic Water

| Preparation 1 | | |
|---|---|---|
| (1) Hydroxypropylated γ-CD | 1.0 | part |
| (2) Benzophenone | 0.05 | part |
| (3) Composed perfumes (limonene, phenylethyl alcohol, citronerol, etc.) | 0.1 | part |
| (4) Deionized water | 3 | part |
| Preparation 2 | | |
| (1) Deionized water | 82.0948 | parts |
| (2) Glycerol | 1.0 | parts |
| (3) 1,3-Butylene glycol | 2.0 | parts |
| (4) Lactic acid | 0.005 | parts |
| (5) Sodium lactate | 0.2 | parts |
| (6) Monoammonium glycyrrhizinate | 0.05 | parts |
| (7) Aloe extract | 0.5 | parts |
| (8) Modified 95% ethanol | 10.0 | parts |
| (9) Dye | 0.0002 | parts |

Preparation Method

To a solution of (1) dissolved in deionized water were added (2) and (3), to prepare the Preparation 1 containing the inclusion product of the hydroxy-propylated γ-CD.

Then the above Preparation 1 was added to the Preparation 2 to obtain a cosmetic water having a UV-absorber and a perfume stably formulated therein.

EXAMPLE 5

Astringent

| Preparation 1 | | |
|---|---|---|
| (1) Hydroxyethylated β-CD | 5.0 | parts |
| (2) Composed perfume (Linanol, Methyldehydrojasmonate, Muskketone, Valinine, etc.) | 0.03 | parts |
| (3) 4-t-Butyl-4'-methoxy-dibenzoylmethane | 0.01 | parts |
| (4) Naphthol yellow | 0.01 | parts |
| (5) Deionized water | 20 | parts |
| Preparation 2 | | |
| (1) Deionized water | 57.57 | parts |
| (2) Dipropylene glycol | 2.0 | parts |
| (3) Citric acid | 0.03 | parts |
| (4) Sodium citrate | 0.05 | parts |
| (5) Zinc sulfophenolate | 0.2 | parts |
| (6) Modified 95% ethanol | 15.0 | parts |
| (7) Methyl p-benzoate | 0.1 | parts |

Preparation Method

To a solution of (1) dissolved in deionized water were added (2), (3), and (4), followed by stirring, to obtain the Preparation 1 containing the inclusion product of the hydroxyethylated β-CD.

Then the above Preparation 1 was added to the Preparation 2 to obtain an astringent having a UV-ray absorber, perfumes, and a dye stably formulated therein.

EXAMPLE 6

Nonalcoholic Cosmetic Water

| Preparation 1 | | |
|---|---|---|
| (1) Hydroxymethylated β-CD | 10 | parts |
| (2) Mentol | 3 | parts |
| (3) Perfume (Rose oil) | 0.01 | parts |
| (4) Deionized water | 20 | parts |
| Preparation 2 | | |
| (1) Deionized water | 56.46 | parts |
| (2) Dipropylene glycol | 10 | parts |
| (3) Citric acid | 0.03 | parts |
| (4) Sodium citrate | 0.05 | parts |
| (5) Methyl p-benzoate | 0.1 | parts |
| (6) Phanoxyethanol | 0.3 | parts |
| (7) Dye | 0.05 | parts |

Preparation Method

To a solution of (1) dissolved in deionized water were added (2) and (3), followed by stirring, to prepare the Preparation 1 containing the inclusion product of the hydroxymethylated β-CD.

Then the above Preparation 1 was added to the Preparation 2 to obtain a nonalcoholic cosmetic water containing an antiphologistic and a perfume stably formulated therein.

EXAMPLE 7

Powder Containing Cosmetic Water

| Preparation 1 | | |
|---|---|---|
| (1) Hydroxybutylated β-CD | 6.0 | parts |
| (2) l-Mentol | 0.3 | parts |
| (3) Camphor | 0.5 | parts |
| (4) Perfume | 0.15 | parts |
| (5) Deionized water | 15 | parts |
| Preparation 2 | | |
| (1) Deionized water | 69.65 | parts |
| (2) Glycerol | 1.0 | parts |
| (3) Asparagine | 0.05 | parts |
| (4) Modified 95% ethanol | 5.0 | parts |
| (5) Zinc | 1.5 | parts |
| (6) Kaolin | 0.5 | parts |
| (7) Methyl p-benzoate | 0.05 | parts |
| (8) Clay mineral | 0.3 | parts |

Preparation Method

To a solution of (1) dissolved in deionized water were added (2), (3), and (4), followed by stirring, to prepare the Preparation 1 containing the inclusion product of the hydroxybutylated β-CD.

Then the above Preparation 1 was added to the Preparation 2 to obtain a powder containing a cosmetic water having an antiphologistic and a perfume formulated stably therein.

EXAMPLE 8

White Powder

| Preparation 1 | | |
|---|---|---|
| (1) Hydroxypropylated CD mixture | 10 | parts |
| (2) Benzophenone | 0.1 | parts |
| (3) 4-t-Butyl-4'-methoxy-dibenzoylmethane | 0.05 | parts |
| (4) Glyceryl dimethoxycinnamate ethylhexanoate | 0.05 | parts |
| (5) Deionized water | 10 | parts |
| Preparation 2 | | |
| (1) D-Mannitol | 64.77 | parts |
| (2) L-Ascorbic acid | 3.0 | parts |
| (3) Dipalmityl ascorbate | 12.0 | parts |
| (4) Monoammonium glycerrhizinate | 0.05 | parts |
| (5) Riboflavin | 0.02 | parts |

Preparation Method

To a solution of (1) dissolved in deionized water were added (2), (3), and (4), followed by stirring, to prepare the Preparation 1 containing the inclusion product of the hydroxypropylated CD mixture. The Preparation 1 was lyophilized to form a powder thereof.

Then the powder of the above Preparation 1 was added to the Preparation 2 to obtain a white powder having a UV-absorber stably formulated therein.

EXAMPLE 9

Essence Powder

| Preparation 1 | |
|---|---|
| (1) Hydroxypropylated CD mixture | 8 parts |
| (2) Evening primrose oil | 0.1 parts |
| (3) α-Tocopherol | 0.05 parts |
| (4) Hyaluronic acid | 0.001 parts |
| (5) Deionized water | 12 parts |
| Preparation 2 | |
| (1) Lactose | 79.849 parts |

Preparation Method

To a solution of (1) and (4) dissolved in deionized water were added (2) and (3), followed by stirring, to prepare the Preparation 1 containing the inclusion product of the hydroxypropylated CD mixture. The Preparation 1 was spray dried to form a powder thereof.

Then the powder of the above Preparation 1 was added to the Preparation 2 to obtain an essence powder having an oil component, an antioxidant, and a humectant stably formulated therein.

EXAMPLE 10

Suncare Powder

| Preparation 1 | |
|---|---|
| (1) Hydroxypropylated α-CD | 4.0 parts |
| (2) Benzophenone | 0.05 parts |
| (3) Deionized water | 6 parts |
| Preparation 2 | |
| (1) Hydroxypropylated β-CD | 4.0 parts |
| (2) 4-t-Butyl-4'-methoxy-dibenzoylmethane | 0.02 parts |
| (3) Glycerol dimethoxycinnamate ethylhexanoate | 0.05 parts |
| (4) p-Aminobenzoic acid ester | 0.5 parts |
| (5) Deionized water | 7 parts |
| Preparation 3 | |
| (1) D-mannitol | 77.349 parts |
| (2) 2-Hydroxy-4-methoxybenzophenone-5-sodium sulfonate | 1.0 parts |
| (3) Uracanic acid | 0.001 parts |
| (4) Monoammonium glycyrrhizinate | 0.03 parts |

Preparation Method

The hydroxypropylated a-CD was dissolved in deionized water and (2) was added to the resultant solution, followed by stirring, to form a UV-ray absorber composite solution, which was then dried to prepare the Preparation 1.

Then the hydroxypropylated β-CD was dissolved in deionized water, and (2), (3) and (4) of the Preparation 2 were added to the resultant solution to form a UV-ray absorber composition solution, which was dried to prepare the Preparation 2.

Further, (1), (2), (3) and (4) of the Preparation 3 were mixed to prepare the Preparation 3, and finally, the Preparation 1 and the Preparation 2 were added to the Preparation 3 to obtain a suncare powder having UV-ray absorbers stably formulated therein.

EXAMPLE 11

Action Against Skin Roughening

Sample of the inclusion products having composed perfume included in CD prepared by dissolving 5 g of various CD or CD derivatives in 95 g of deionized water and adding 0.01 g of a composed perfume (linalol, linalol acetate, lavender oil, santalol, coumarine, etc.), followed by stirring, were used to determine the skin roughening prevention effect.

The hair at the back of 3 Hartley-strain guinea pigs weighing 700 to 850 g was cut with a pair of clippers, followed by a of depilation treatment. On day 4 after the hair was removed, 25 ml of an aqueous 3% sodium alkylbenzenesulfonate (LAS) solution was continuously applied once per day on 4 sites of the skin to which the depilation treatment was applied to cause skin roughening. Further, at the same sites, after coating the LAS solution, 50 ml of each of the above mentioned samples was applied once per day.

The changes in the state of the skin on day 7 after the initiation of the LAS aqueous solution application were evaluated with regard to erythema and exfoliation according to the standards shown below; these are average values. Also, the totals of the respective average values of erythema and exfoliation are shown as the skin roughening score. The results are shown in Table 2.

| Evaluation of Erythema | |
|---|---|
| Score | Change |
| 0 | No change |
| 0.5 | Rubor slightly recognized |
| 1 | Rubor recognized from state of skin surface |
| 2 | Rubor and edema recognized from state of skin surface |
| 3 | Rubor, edema and erosion recognized from state of skin surface |
| 4 | Rubor, edema, erosion and ulcer recognized from state of skin surface |

| Evaluation of exfoliation | |
|---|---|
| Score | Change |
| 0 | No change |
| 0.5 | Slight drying, but no exfoliation |
| 1 | Slight exfoliation |
| 2 | Moderate exfoliation |
| 3 | Heavy exfoliation |

TABLE 2

| Sample | Erythema | Exfoliation | Skin roughening score (Total) | Remark |
|---|---|---|---|---|
| Hydroxypropyl-β-CD | 0.2 | 0.6 | 0.8 | Invention |
| α-CD | 0.7 | 2.0 | 2.7 | Comparison |
| β-CD | 0.9 | 0.7 | 1.6 | " |
| γ-CD | 0.5 | 1.1 | 1.6 | " |
| β-CD-polymer | 1.1 | 1.2 | 2.3 | " |

Although the skin roughening prevention effect is greatest as the numerical value of skin roughening score

EXAMPLE 12

Action of Corneum Turnover

To determine the effect on turnover of corneum, the respective samples were applied in the same manner as in Example 1 except that duncil chloride was applied on the same sites before the application of the 3% aqueous DAS solution of Example 11. From the change of a relative fluorescent value with a lapse of time, the days when only 50% of the original fluorescent value appeared were calculated. The results are shown in Table 3. The turnover of corneum is accelerated as the days in which 50% of the fluorescence disappears are lessened, suggesting progress against the skin roughening.

TABLE 3

| Sample | 50% fluorescence disappearance days | Remark |
| --- | --- | --- |
| Hydroxypropyl-$\beta$-CD | 4.7 | Invention |
| $\alpha$-CD | 3.8 | Comparison |
| $\beta$-CD | 3.4 | " |
| $\gamma$-CD | 3.7 | " |
| $\beta$-CD-polymer | 2.7 | " |

As apparent from Table 3, hydroxpropyl-$\beta$-CD of the present invention is very effectively inhibits the corneum turnover, compared with the samples formulated for comparative purposes.

We claim:

1. A cosmetic composition consisting essentially of an inclusion product having a slightly water-soluble component and a hydroxypropyl-$\beta$-cyclodextrin, said slightly water-soluble component being at least one member selected from the group consisting of an UV-ray absorber, a preservative and perfume, wherein the content of the inclusion product in the cosmetic composition is an effective amount up to 25% by weight.

2. A cosmetic composition as claimed in claim 1, wherein the content of the inclusion product in the cosmetic composition is 0.5 to 15% by weight.

3. A liquid composition of claim 1.

4. A powdery composition of claim 1.

5. A cosmetic composition as claimed in claim 1, wherein said slightly water-soluble component is an UV-ray absorber selected from the group consisting of benzophenone, 4-t-butyl-4'-methoxydibenzoylmethane, octyl p-methoxycinnamate and p-aminobenzoate.

6. A cosmetic composition as claimed in claim 1, wherein said slightly water-soluble component includes a preservative selected from the group consisting of methyl p-benzoate, ethyl p-benzoate, propyl p-benzoate and butyl p-benzoate.

7. A cosmetic composition as claimed in claim 1, wherein said slightly water-soluble component is a perfume selected from the group consisting of linalool, linalyl acetate, limonene, citral, menthyl lionone, benzyl acetate, methyldehydrojasmonate, phenylethyl alcohol, musketone, santalol, $\alpha$-hexylcinnamicaldehyde, TEC, citronelol, and composed perfumes comprising mixtures thereof and essential oils derived from natural animal and vegetable oils and fats, and galenicals.

8. A cosmetic composition as claimed in claim 7, wherein the hydroxypropyl-$\beta$-cyclodextrin is present in about 5% by weight.

9. A composition according to claim 1, wherein the inclusion product is present in finely powdered state.

* * * * *